United States Patent [19]

Heyman

[11] Patent Number: 4,893,621
[45] Date of Patent: Jan. 16, 1990

[54] SLIPOVER ANTEGRADE LOADING CALCULUS EXTRACTION INSTRUMENT SYSTEM

[76] Inventor: Arnold M. Heyman, 2071 W. Alameda Ave., Ste. 406, Burbank, Calif. 91505

[21] Appl. No.: 899,669

[22] Filed: Aug. 22, 1986

[51] Int. Cl.⁴ ............................................. A61B 17/00
[52] U.S. Cl. ....................................... 606/127; 604/54
[58] Field of Search ................... 128/328, 303 R, 320, 128/323, 324, 348.1, 356, 737; 604/105, 49, 54

[56] References Cited

U.S. PATENT DOCUMENTS

| | | | |
|---|---|---|---|
| 2,943,626 | 7/1960 | Dormia | 128/328 |
| 3,886,933 | 6/1975 | Mori et al. | 128/328 |
| 4,203,429 | 5/1980 | Vasilevsky et al. | 128/328 |
| 4,590,938 | 5/1986 | Segura et al. | 128/328 |
| 4,643,184 | 2/1987 | Mobin-Uddin | 128/303 R |

OTHER PUBLICATIONS

*Catheters & Accessories Cardiology–Radiology*, United States Catheter & Instrument Corp., New York, 1964, p. 32.

Primary Examiner—C. Fred Rosenbaum
Assistant Examiner—Denise Whelton
Attorney, Agent, or Firm—Spensley Horn Jubas & Lubitz

[57] ABSTRACT

Ureteral stones or calculi may be extracted with a minimum amount of risk of trauma and damage to the ureter by use of the present invention's slipover extraction device. The present invention first positions a guide wire beyond the ureteral stone. An open-end, hollow catheter is then slid coaxially along the guide wire to be also positioned beyond the stone. After the guide wire is removed, a stone basket is slid coaxially within the catheter, where it is also positioned beyond the stone for extraction.

7 Claims, 3 Drawing Sheets

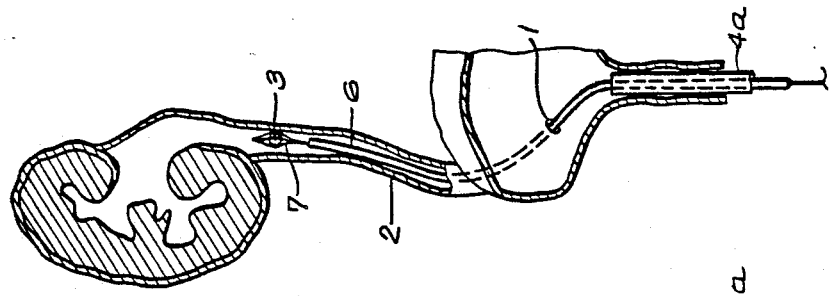
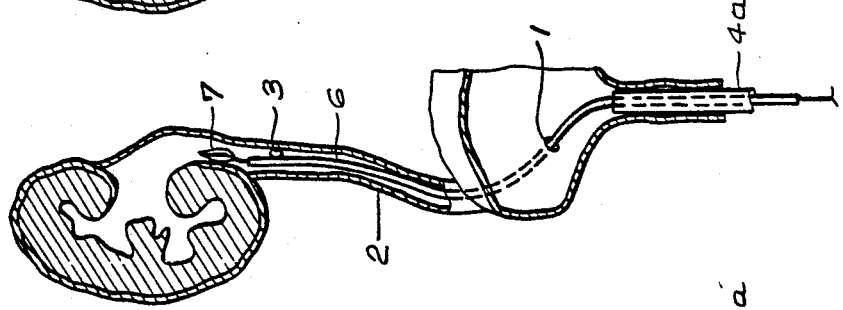
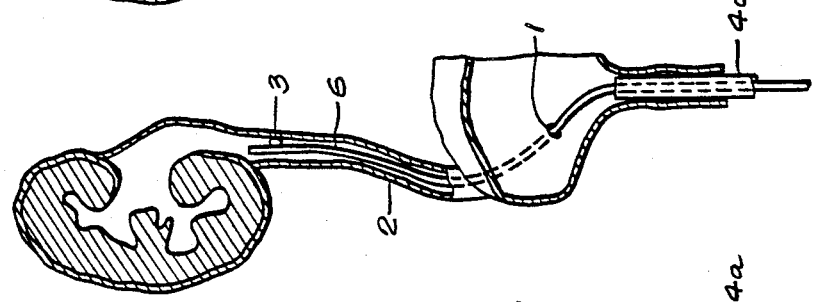
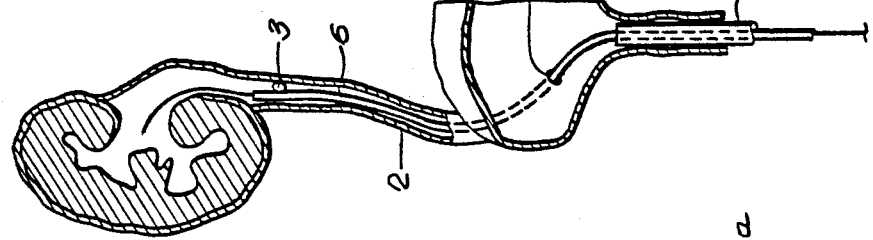
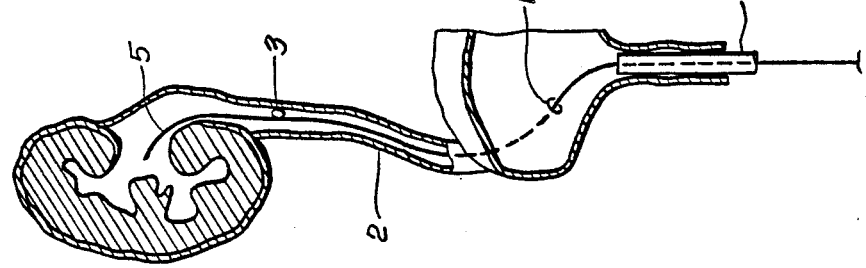

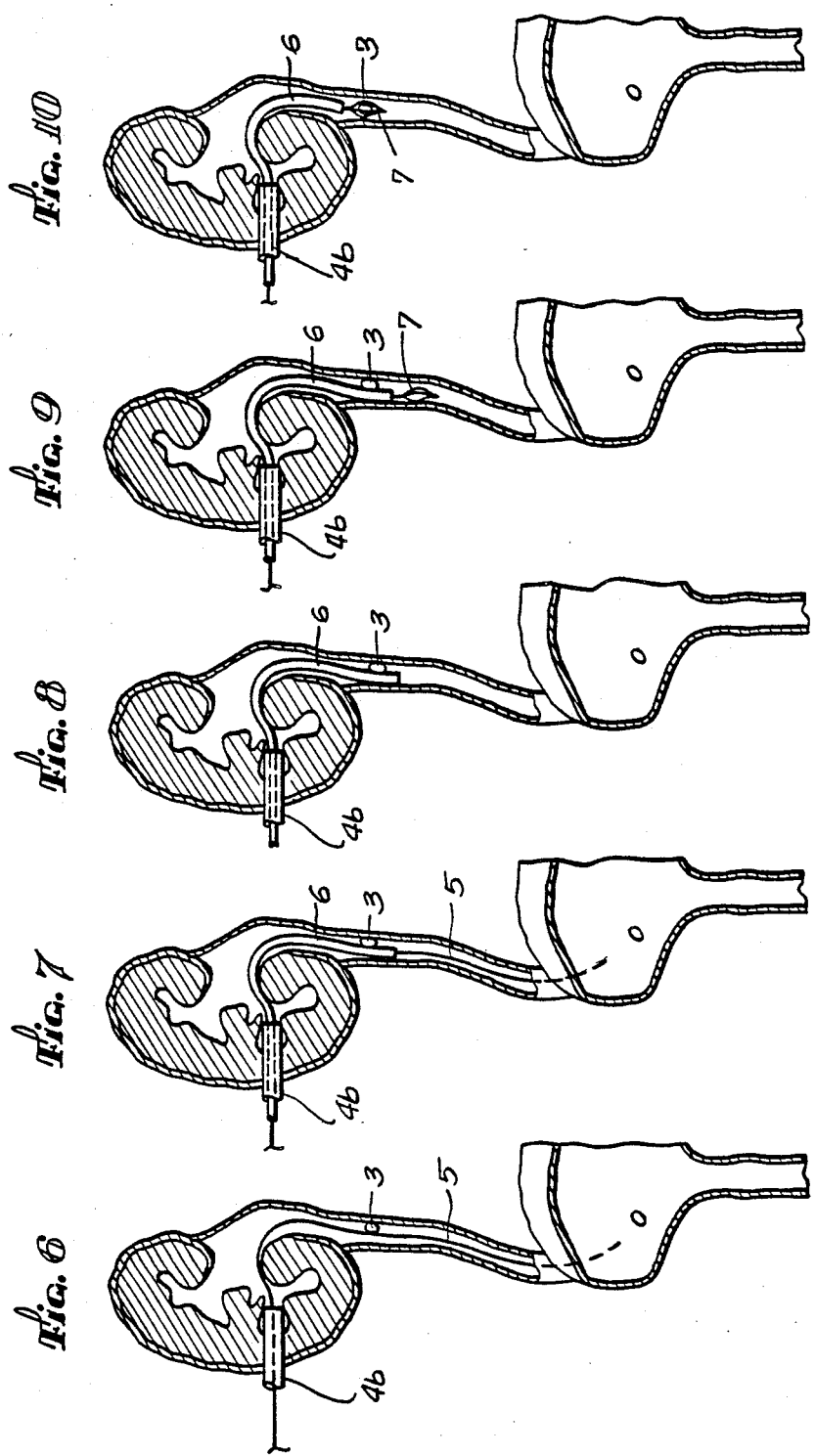

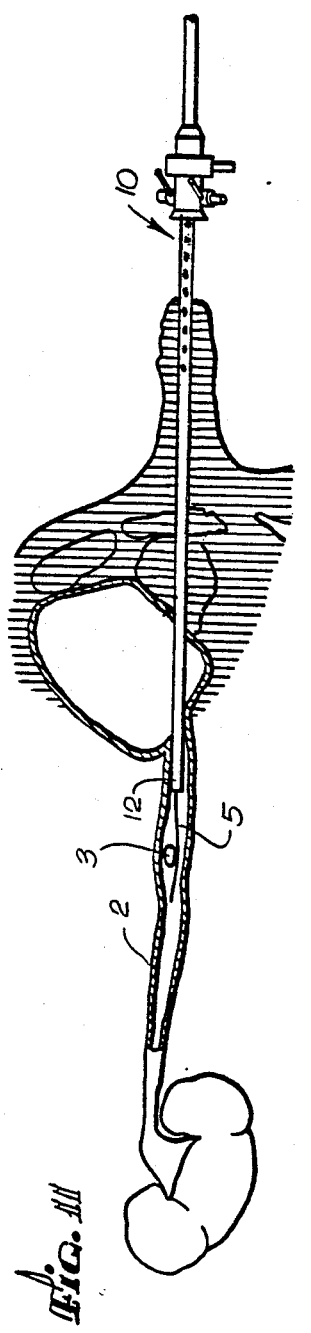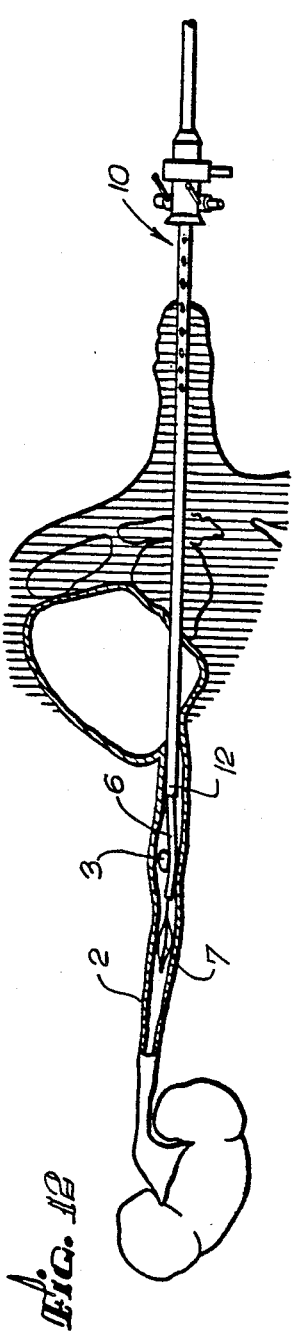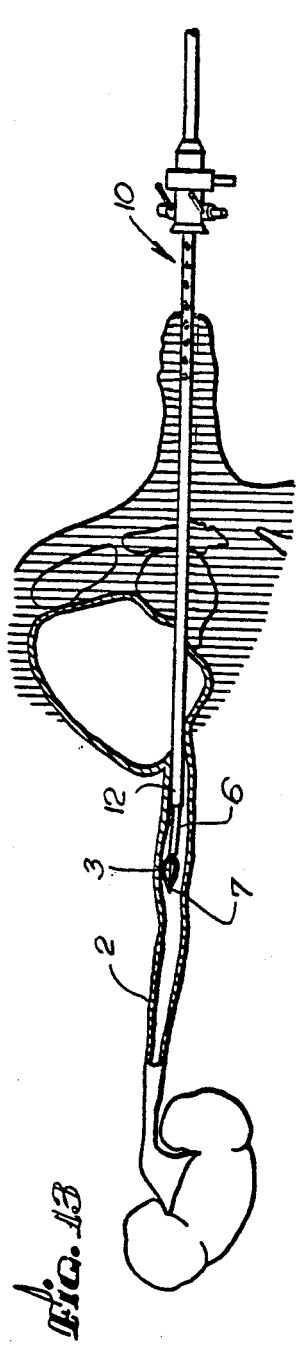

SLIPOVER ANTEGRADE LOADING CALCULUS EXTRACTION INSTRUMENT SYSTEM

BACKGROUND OF THE INVENTION

The present invention relates to a medical instrument system for removing foreign objects from a tubular body, more particular, to an instrument system used for extraction of stones or calculi that may be obstructing the ureter.

The ureter is a narrow mucous-lined tubular canal connecting the kidney and bladder for the passage of urine. Stones are formed in the kidney and may pass down through the ureter to the bladder, then are usually voided naturally through the urethra. These calculi occasionally become trapped in the ureter because of irregular barbed surfaces of the calculi or for other reasons such as normal and pathological narrowing of the ureter. As a result, they remain in the ureter and may obstruct the passage of urine. The resultant accumulating back pressure of urine may then cause impaired function of the kidney, infection, or intense pain and discomfort to the patient. One acceptable method of removing the obstruction is to endoscopically remove the stone by capturing it with an instrument inserted through the ureter. One prior technique of this method involved using a cystoscope introduced into the bladder and passing up the ureter toward the stone, a non-sheathed umbrella-like instrument, which is called a stone basket. This basket would be passed beyond the stone and once upstream from the stone, the basket would be pulled downstream in order to capture the stone in its webbing and then extract it. An example of such a stone basket is illustrated in the 1948 BARD Catalogue, No. 344-Johnson Stone Basket.

Another prior art device is a sheath basket in which the metal wire webbing basket is positioned within a hollow tubular catheter therefore sheathing the otherwise exposed wires. In this manner, the operator passes a sheathed stone basket up the ureter beyond the stone. At that point, the operator would push the stone basket up and out the distal end of the catheter, opening the basket, and then manipulating the basket down-stream in order to try to capture the stone and extract it in the basket.

As with both the sheath and non-sheathed baskets, there is a great danger to the ureter in passing these instruments. They may cause trauma and damage to the ureter especially if forced through the constricted or swollen ureteral area around the stone. The danger of trauma to the ureter by a ureteral instrument device cannot be overemphasized, if the ureteral device injures the ureter, the device itself may become imbedded and trapped in the ureter or may tear the ureter while trying to extricate it. In that event, full scale surgery with its inherent morbidity and mortality is then required to repair the ureter and/or to remove the device and to remove the stone.

These sheathed and non-sheathed stone baskets of the prior arts are relatively large in diameter, although they are somewhat smaller than the inside diameter of the ureter. More recently, in the instrumentation of the ureter there has come to be a guide wire, which is used to traverse the ureter. This is much smaller than the stone baskets and is much safer. A most recent prior art device is now being used which is the Carson Stone Basket. This was described in an article printed in the October 1984 edition of "Urology". The Carson Basket slides over the previously inserted guide wire which has already passed the stone. It is obvious that if the guide wire is in place it is much easier and safer to pass the stone basket beyond the calculus. The only problem with the Carson device is it still has the exposed wire webbing which may be a hazard to the ureter in its passage.

As a result, there still remains, with the use of all the prior art devices, a high possibility of accidental trauma caused by the stone basket's probing the narrow passageway between the stone and the ureter. The object of the present invention is to provide a method and system of removing the ureteral stones by minimizing the risk of ureteral trauma.

With the advent of the percutaneous approach to the kidney, ureteral calculi have now been approached antigrade from the kidney down the ureter. Because of the need to retain a safety guide wire in place during the procedure, in the present invention a second guide wire would be passed down the ureter and beyond the stone. Then a sheath would be percutaneously passed over the second guide wire down the ureter until it was below the calculus. The guide wire would then be removed and the stone basket would be loaded antigrade into the sheath and passed down the ureter and beyond the stone. The stone basket would be opened beyond the stone and brought back up the ureter until it engaged the stone and then extracted it.

Another recent development is the use of a ureteroscope which gives direct visualization within the ureter, permitting one to directly observe the calculus while extracting it. The device of the present invention can be used in combination with the ureteroscope so that the extraction can be performed under direct visualization. This enables extraction of calculus with substantially less risk and trauma. The instrument described herein is designed to take advantage of the ability to pass guide wires down antigrade from the kidney percutaneously into the ureter.

SUMMARY OF THE INVENTION

In accordance with the present invention, the above objective may be achieved by employing a system which utilizes a guide wire, a slip-over catheter, and an antigrade loading slip-through stone basket. The present invention employs the use of a guide wire, a familiar endourological technique. The problems thus associated with the other stone baskets are substantially eliminated as the guide wire is much more easily passed up the ureter beyond the stone obstruction. Once the guide wire is beyond the stone, one may now easily pass a catheter coaxially antigrade over the guide wire beyond the stone. At this point, the guide wire may now be removed as the catheter is in proper position beyond the stone. The stone basket may then be passed coaxially within the catheter into position beyond the stone safely, without any danger of trauma, for the extraction of the stone.

BRIEF DESCRIPTION OF THE DRAWINGS

A detailed description of the invention will be made with reference to the accompanying drawings, wherein like numerals designate corresponding parts in the several figures.

FIG. 1 shows the first step of the present invention's system of extraction of ureteral stones, wherein a guide wire is manipulated through the a cystoscope in the bladder, up the ureter, and beyond the lodged stone.

FIG. 2 shows the second step of the system, wherein a catheter is coaxially passed along the guide wire up the ureter and is positioned beyond the stone.

FIG. 3 shows the third step of the system, wherein the guide wire is removed.

FIG. 4 shows the fourth step of the present invention's system, wherein a stone basket is guided up antegrade within the catheter in this position beyond the stone for its capture.

FIG. 5 shows the final step of the present invention's system wherein the stone basket has captured the stone for extraction.

FIGS. 6-10 show another use of the present invention, wherein the invention's method and system is used percutaneously with percutaneous access to the kidney to permit the extraction of upper uretral calculi. In this case, antegrade extraction is performed by percutaneously inserting a guide wire from the kidney down through the ureter and beyond the stone. FIGS. 6-10 correspond respectively to the same steps demonstrated in FIGS. 1-5.

FIGS. 11-13 show another use of the present invention wherein the invention's method and system is used with a uretero-renoscope.

DESCRIPTION OF THE PREFERRED EMOBODIMENT

The following detailed description is of the best presently contemplated mode of carrying out the invention. This description is not to be taken in a limiting sense, but is made merely for the purpose of illustrating the general principles of the invention. The scope of the invention is best defined by the appended claims.

In its preferred embodiment, the present invention is to be used as a system for the extraction of stones or calculi lodged in the ureter. The present invention's system utilizes a guide wire 5, a slip-over catheter 6, and a slip-through wire stone basket 7.

In accordance with the preferred embodiment, the present invention uses a linear thin guide wire 5 whose length is approximately 50 to 60 centimeters long and whose outer diameter is 0.038 mm. Although other guide wires measuring different diameters may be used, a 0.038 mm size is seen to be preferable as it is small enough for manipulating around the stone and yet large enough for easy manipulation. In addition, the guide wire is flexible, preferably has a soft bendable tip, and is teflon coated.

The present invention furthermore uses a hollow catheter for the coaxial passage of the stone basket through the catheter. The choice of the internal diameter of the hollow catheter to be used depends on the outer diameter of the selected stone basket to be inserted within the catheter. Preferably, an internal diameter is chosen which just permits the stone basket to be easily manipulated through the catheter. In that way, the catheter's outer diameter is minimized, thereby simplifying its manipulation within the ureter.

The choice of outside diameter of the hollow catheter should also be small enough to pass through the channel of ureteroscope. The catheter is also open at its distal end to permit the stone basket to be extended out beyond the end of the catheter.

The operation of the present invention's medical instrument system will now be explained. Referring to FIG. 1, guide wire 5 is positioned into the urerteral opening 1 in the bladder with the aid of a cystocope 4a. The guide wire 5 is then advanced up the ureter 2 and beyond a lodged stone or calculi 3. In FIG. 2, a slip-over, open-end hollow catheter 6 is slid coaxially along guide wire 5 and up the ureter to be positioned beyond the stone 3. FIG. 3 shows the guide wire 5 removed, leaving the catheter 6 in place beyond the stone 3. In FIG. 4, the slip-through wire stone basket 7 has been passed coaxially within the catheter 6 and out through the catheter's open end, thereby positioning the stone basket 7 beyond stone 3. FIG. 5 shows the actual capture of stone 3 by manipulating and retracting stone basket 7.

As shown in FIGS. 6-10, the present invention's system may also be used percutaneously to remove upper uretal stones or calculi whereby a guide wire 5 is surgically inserted into the kidney and through the urethra beyond a lodged stone with the aid of a nephroscope 4b. The antegrade extraction of stone 3 then proceeds exactly as described earlier.

Specifically, FIG. 6 shows guide wire 5 inserted through a nephroscope 4b from the kidney, into the upper portion of the ureter 2 and positioned down beyond a lodged stone or calculi 3. A slip-over, openend hollow catheter 6 is then slid coaxially over the guide wire 5 and down the ureter to be positioned beyond stone 3 as shown in FIG. 7. FIG. 8 shows the guide wire 5 removed, leaving the catheter 6 in place beyond stone 3. In FIG. 9, the slip-through wire stone basket 7 has been passed coaxially within the catheter 6 and out through the catheter's open end, thereby positioning the stone basket 7 beyond stone 3. FIG. 10 shows the actual capture of stone 3 by manipulating and retracting stone basket 7.

A third embodiment is illustrated in FIGS. 11 through 13 which illustrates the use of a ureterorenoscope 10. Such a device is well known in the art and is inserted through the penis under direct vision and up the ureter. In the present invention, scope 10 is directed through the urethra and bladder and into the ureter 2. The tip 12 of the scope 10 is positioned into the ureter 2 just below the stone 3. Guide wire 5 is then passed through the scope 10 beyond the stone 3 as explained above. As illustrated in FIG. 12, catheter 6 is then passed through the scope 10 using the wire 5 as a guide to get beyond stone 3. The wire 5 is then removed and a stone basket 7 is passed through the catheter 6. The basket is now pulled back toward tip 12 of scope 10 and the stone 3 is captured as illustrated in FIG. 13 under direct vision.

In accordance with the preferred embodiment, the present invention provides a novel method and system of removing ureteral stones that minimizes the risk of ureteral trauma present in the prior art systems and methods. The above description of the presently preferred embodiment of the invention was intended to illustrate by way of example the novel features that are believed to be characteristics of the present invention. It is to be expressly understood, however, that the specific embodiment is for the purpose of illustration and description only and is not intended as a definition of the limits of the invention. Other possible embodiments and applications of the invention are included within the scope of the invention.

What is claimed is:

1. A method for passing a medical instrument system through a ureter and beyond a lodged foreign body, said medical instrument system comprising:

a flexible thin guide with a fine soft bendable tip for passing along said tubular body beyond said lodged foreign body;

an elongated hollow tubular catheter, said catheter having an inner diameter larger than said outer diameter of said guide and adapted to be passed over said guide, and beyond said lodged foreign body; and an umbrella like stone basket, said basket having open and closed modes, said closed mode being when said basket has its smallest cross-sectional area, said open mode being when said basket has its largest cross-sectional area, when open said basket configured to entangle and extract lodged foreign bodies in an antegrade manner and when closed said basket configured to pass through and within said catheter and exit from said catheter; the method comprising the steps of:

passing said guide through said tubular body beyond said lodged foreign body;

coaxially sliding said catheter over said guide up said ureter to be positioned beyond said lodged foreign body;

removing said guide; and passing coaxially within said positioned catheter said stone basket to be positioned beyond said foreign body for its extraction, said basket being in a closed position as it proceeds through said catheter.

2. A method for passing a medical instrument system as claimed in claim 1 wherein said stone basket is used to entangle and extract said lodged foreign body.

3. A method for extracting a foreign body lodged in a membranous tubular body, the steps of the method comprising:

passing a guide along and within the tubular body, between the foreign body and an interior wall of the tubular body and beyond the foreign body;

passing a hollow catheter coaxially along and over the guide between the foreign body and the interior wall of the tubular body and beyond the foreign body;

passing an extracting means for removing the foreign body from the tubular body through and along the interior of the hollow catheter between the foreign body and the interior wall of the tubular body and beyond the foreign body, such that the extracting means exits the hollow catheter and is exposed to the tubular body only after passing beyond the foreign body; and extracting the foreign body from the tubular body.

4. The method of claim 3 wherein the guide is a guide wire.

5. The method of claim 3 wherein the extracting means comprises an umbrella-like stone basket, said basket being capable of entangling and extracting the lodged foreign body.

6. The method of claim 5 wherein the extracting step comprises withdrawing the stone basket and catheter together.

7. The method of claim 3 further comprising the step of removing the guide from the hollow catheter prior to passing the extracting means through and along the interior of said hollow catheter.

* * * * *